(12) United States Patent
Tanaka et al.

(10) Patent No.: US 10,379,039 B2
(45) Date of Patent: Aug. 13, 2019

(54) NDIR GAS SENSOR, GAS ANALYZER, PHOTOSYNTHESIS RATE MEASURING APPARATUS, AND PHOTOSYNTHESIS RATE MEASURING METHOD

(71) Applicants: Kyoto University, Kyoto (JP); Masa International Corp., Kyoto- (JP)

(72) Inventors: Yu Tanaka, Kyoto (JP); Shigeyuki Akiyama, Kyoto (JP)

(73) Assignees: Kyoto University, Kyoto (JP); Masa International Corp., Kyoto (JP)

( * ) Notice: Subject to any disclaimer, the term of this patent is extended or adjusted under 35 U.S.C. 154(b) by 0 days.

(21) Appl. No.: 15/736,321

(22) PCT Filed: Jun. 10, 2016

(86) PCT No.: PCT/JP2016/067391
§ 371 (c)(1),
(2) Date: Dec. 14, 2017

(87) PCT Pub. No.: WO2016/208424
PCT Pub. Date: Dec. 29, 2016

(65) Prior Publication Data
US 2018/0188162 A1    Jul. 5, 2018

(30) Foreign Application Priority Data

Jun. 22, 2015 (JP) ................. 2015-124727

(51) Int. Cl.
*G01N 21/3504* (2014.01)
*G01N 33/00* (2006.01)
*G01N 21/84* (2006.01)

(52) U.S. Cl.
CPC ....... *G01N 21/3504* (2013.01); *G01N 33/004* (2013.01); *G01N 33/0098* (2013.01);
(Continued)

(58) Field of Classification Search
CPC ............ G01N 21/3504; G01N 33/004; G01N 33/0098; G01N 2021/8466;
(Continued)

(56) References Cited

U.S. PATENT DOCUMENTS 4,803,370 A   2/1989 Eckles
2017/0118925 A1* 5/2017 Noguchi ................ G06Q 50/02

FOREIGN PATENT DOCUMENTS

JP   61-108947   5/1986
JP   08-172913   7/1996
(Continued)

OTHER PUBLICATIONS

Long, "Measurement of Leaf and Canopy Photosynthetic CO2 Exchange in the Field", Journal of Experimental Botany, vol. 47, No. 304, pp. 1629-1642, Nov. 1, 1996.
(Continued)

*Primary Examiner* — David P Porta
*Assistant Examiner* — Meenakshi S Sahu
(74) *Attorney, Agent, or Firm* — Kirschstein, Israel, Schiffmiller & Pieroni, P.C.

(57) ABSTRACT

An NDIR gas sensor has high responsiveness and less noise and includes a radiating section arranged to radiate an infrared ray, a detecting section arranged to detect the infrared ray radiated by the radiating section, and a sample cell extending between the radiating section and the detecting section along a route of the infrared ray and covering the entire circumference of the route of the infrared ray. The sample cell includes a plurality of cell elements extending along the route of the infrared ray. Side portions of the cell elements adjacent to each other overlap at an interval from each other.

10 Claims, 9 Drawing Sheets

(52) U.S. Cl.
CPC ............... *G01N 2021/8466* (2013.01); *G01N 2201/023* (2013.01)

(58) Field of Classification Search
CPC .. G01N 2201/023; A01G 9/247; A01G 22/00; A01G 7/00
USPC ...................................................... 250/341.1
See application file for complete search history.

(56) References Cited

FOREIGN PATENT DOCUMENTS

| | | |
|---|---|---|
| JP | 2009-014585 | 1/2009 |
| JP | 2009-139215 | 6/2009 |
| JP | 2011-169633 | 9/2011 |
| JP | 2013-221804 | 10/2013 |

OTHER PUBLICATIONS

Tamayo, "Gas Exchange Techniques in Photosynthesis and Respiration Infrared Gas Analyser", http://www.sfrc.ufl.edu/courses/BOT6935/handouts/Ramos Tamayo 2001.pdf (retrieved Oct. 9, 2017), pp. 113-139, Jan. 1, 2001.
Mitchell, "Measurement of Photosynthetic Gas Exchange in Controlled Environments", Hortscience, vol. 27, No. 7, pp. 764-767, Jul. 1, 1992.
Holsteijn, "A Closed System for Measurement of Photosynthesis, Respiration and CO2 Compensation Points", Mededelingen Landbouwhogeschool Wageningen, pub. 459, pp. 1-14, Jan. 1, 1979.
European Search Report in corresponding European application No. 16814195.0, dated Nov. 6, 2018.
International Search Report in corresponding international application No. PCT/JP2016/067391, dated Aug. 23, 2016.

\* cited by examiner

$t_0$ : Zero gas injection start time
$t_1$ : 90% Response reaching time
Response time $T_{90} = t_1 - t_0$

NDIR GAS SENSOR, GAS ANALYZER, PHOTOSYNTHESIS RATE MEASURING APPARATUS, AND PHOTOSYNTHESIS RATE MEASURING METHOD

TECHNICAL FIELD

The present invention relates to an NDIR gas sensor for gas detection or gas concentration measurement, a gas analyzer including the NDIR gas sensor, and a photosynthesis rate measuring apparatus including the gas analyzer. Further, the present invention relates to a photosynthesis rate measuring method for measuring a photosynthesis rate using the gas analyzer.

BACKGROUND ART

A plant absorbs $CO_2$ and performs photosynthesis. Therefore, in general, a photosynthesis rate of the plant is measured on the basis of $CO_2$ concentration under an environment in which the measurement target plant is present (e.g., Patent Literature 1).

Figure 10:
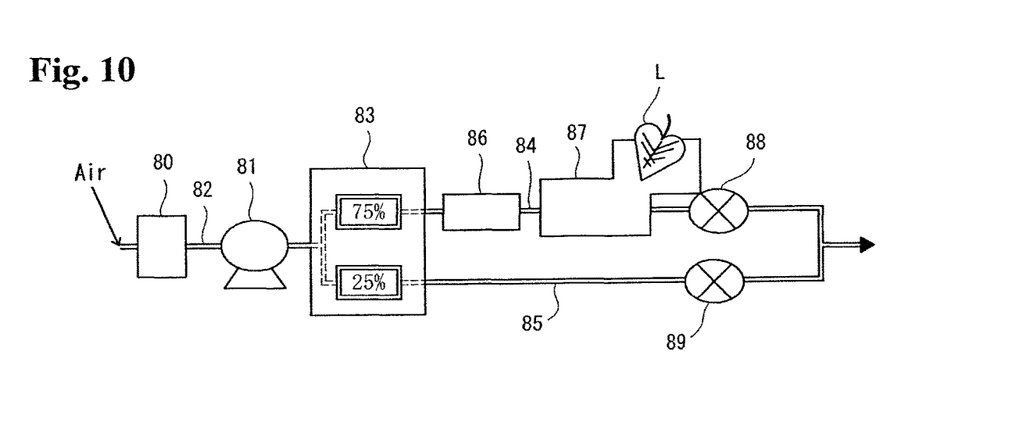
FIG. 10 is a diagram for explaining an apparatus and a method for photosynthesis rate measurement in the prior art.

An apparatus and a method for measurement of a photosynthesis rate in the prior art are shown in FIG. 10. The air is introduced into an introduction line 82 by a pump 81 and, after passing the filter 80, sent to a flow-rate control section 83. The flow-rate control section 83 feeds a constant percentage (e.g., 75%) of the air into a sample line 84 as a sample gas and feeds the remaining (25%) air into a reference line 85 as a reference gas at a constant rate.

The sample gas passes through a flow meter 86, a chamber 87, and a gas analyzer 88 in order. In the chamber 87, light is radiated from a light source on a leaf L serving as a measurement target (hereinafter referred to as measurement leaf). The measurement leaf L absorbs $CO_2$ of the sample gas in the chamber 87 and performs photosynthesis. $CO_2$ concentration reduced by the photosynthesis is measured by the gas analyzer 88 downstream of the chamber 87.

In the reference line 85, the reference gas passes through a gas analyzer 89. At that time, $CO_2$ concentration of the reference gas is measured by the gas analyzer 89.

A difference between the $CO_2$ concentration of the reference gas and the $CO_2$ concentration of the sample gas is calculated. A photosynthesis rate is obtained by multiplying the difference with a flow rate of the sample gas measured by the flow meter 86.

CITATION LIST

Patent Literature

Patent Literature 1: Japanese Patent Application Laid-Open No. H8-172913
Patent Literature 2: Japanese Patent Application Laid-Open No. 2011-169633

SUMMARY OF INVENTION

Technical Problem

The $CO_2$ concentration reduced by the photosynthesis is measured while the sample gas is fed into the chamber 87. This is a state in which, whereas the $CO_2$ concentration of the sample gas in the vicinity of the rear surface of the measurement leaf L is reduced by the photosynthesis, the air continues to flow into the chamber 87. Therefore, it takes time until a dynamic balance of the $CO_2$ concentration stabilizes. This means that it takes time until the $CO_2$ concentration measured by the gas analyzer 88 stabilizes. Usually, even when the gas concentration of the air is stable, at least approximately 2 minutes are required. Therefore, an extremely long time is required for measuring a photosynthesis rate.

The $CO_2$ concentration being measured by the gas analyzer 88 gradually decreases and stabilizes. Therefore, difficulty in determining whether the $CO_2$ concentration is in a stable state is also a factor of the long measurement time. As a method of reducing the measurement time, a method of increasing a flow rate is conceivable. However, when the flow rate is increased, measurement accuracy is deteriorated, since a change in the $CO_2$ concentration decreases.

Further, there are a lot of error factors and the measurement accuracy is low. Accurate measurement cannot be performed unless response speeds of the two gas analyzers 88 and 89 are set almost the same. As the error factors, there are a baseline error due to instability of the air concentration, a performance error (zero drift, span drift, reading reproducibility, etc.) of the two gas analyzers 88 and 89, and a flow rate error due to instability of flow rate control such as inability to feed the sample gas at a constant flow rate.

Since the large pump 81, the flow-rate control section 83, the flow meter 84, and the two gas analyzers 88 and 89 are required, an increase in the size of the apparatus cannot be avoided.

Besides, a method of causing a measurement leaf to absorb $CO_2$ contained in a sealed chamber and measuring decreasing $CO_2$ concentration in the chamber with an NDIR (non-dispersive infrared ray) gas sensor on a real-time basis to thereby calculate a photosynthesis rate has been considered. However, this method cannot be carried out because of low responsiveness of the gas sensor.

A cause of the low responsiveness is the structure of a sample cell of the gas sensor. As explained in Patent Literature 2, the sample cell includes a cylindrical main body section and two tube sections connected to the circumferential wall of the main body section. The sample gas is introduced into the main body section through one tube section and discharged to the outside through the other tube section. While the sample gas passes through the main body section, concentration of a target gas included in the sample gas is measured. In this configuration, since gas in the chamber is not instantaneously introduced into the sample cell, the concentration of $CO_2$ is not measured on a real-time basis and accurately.

Besides the sample cell, Patent Literature 2 discloses a sample cell having an outer circumferential wall in which a large number of holes are formed. With this configuration, since gas is instantaneously introduced into the sample cell, high responsiveness is obtained. However, the sample cell cannot cover an entire circumference of a route of an infrared ray because of the holes of the sample cell. Therefore, environmental light can easily enter the sample cell through the holes. Consequently, there is a lot of noise and accurate measurement cannot be performed.

The present invention provides an NDIR gas sensor having high responsiveness and less noise and a gas analyzer including the gas sensor. Further, the present invention provides a photosynthesis rate measuring apparatus having a short measurement time and high measurement accuracy and capable of being reduced in size. Further, the present invention provides a photosynthesis rate measuring method having a short measurement time and high measurement accuracy.

Solution to Problem

The present invention provides an NDIR gas sensor for gas detection or gas concentration measurement, the NDIR gas sensor including: a radiating section arranged to radiate an infrared ray; a detecting section arranged to detect the infrared ray radiated by the radiating section; and a sample cell extending between the radiating section and the detecting section along a route of the infrared ray and covering an entire circumference of the route. The sample cell includes a plurality of cell elements extending along the route. Side portions of the cell elements adjacent to each other overlap at an interval from each other.

The sample cell may have a shape tapered from the radiating section toward the detecting section. Each of the cell elements may have an inner surface plated with gold or mirror-finished.

In one embodiment, the sample cell includes a first cell element and a second cell element. One side portion of the first cell element and one side portion of the second cell element overlap at an interval from each other to form a first gap extending along the route. The other side portion of the first cell element and the other side portion of the second cell element overlap at an interval from each other to form a second gap extending along the route.

The present invention provides a gas analyzer used for measurement of a photosynthesis rate of a measurement leaf, the gas analyzer including: a sealable chamber including an opening to be closed by the measurement leaf; a fan arranged in the chamber to circulates gas in the chamber; and the NDIR gas sensor arranged to measure $CO_2$ concentration in the chamber.

The gas analyzer may further include a light source arranged to radiate light on the measurement leaf. The opening of the chamber may face upward. The fan may be arranged right under the opening of the chamber. The NDIR gas sensor may be arranged right under the fan.

The fan may be arranged in the chamber to generate an air current flowing toward the opening of the chamber. Instead, the fan may be arranged in the chamber to generate an air current flowing toward a direction opposite to the opening of the chamber.

The gas analyzer according to the present invention may be used for uses other than the photosynthesis rate measurement. In another embodiment, the gas analyzer includes: a chamber; an introduction line connected to the chamber so as to introduce a sample gas into the chamber, a discharge line connected to the chamber so as to discharge the sample gas from the chamber, and the NDIR gas sensor arranged to detect a target gas in the sample gas introduced into the chamber or to measure concentration of the target gas.

The present invention provides a photosynthesis rate measuring apparatus for measuring a photosynthesis rate of a measurement leaf, the photosynthesis rate measuring apparatus including: the gas analyzer for photosynthesis rate measurement; and a rate calculating section configured to calculate a photosynthesis rate of the measurement leaf on the basis of a temporal change of the $CO_2$ concentration measured by the gas analyzer.

The present invention provides a photosynthesis rate measuring method for measuring a photosynthesis rate of a measurement leaf, the photosynthesis rate measuring method including: preparing the gas analyzer for photosynthesis rate measurement; closing the opening of the chamber with the measurement leaf and sealing the chamber; measuring $CO_2$ concentration in the chamber with the NDIR gas sensor while causing the measurement leaf to perform photosynthesis and circulating gas in the chamber with the fan; and calculating a photosynthesis rate of the measurement leaf on the basis of a temporal change of the measured $CO_2$ concentration.

In the method, it is preferable that the photosynthesis rate of the measurement leaf is measured on the basis of the temporal change of the $CO_2$ concentration in the chamber within 10 seconds from a photosynthesis start.

Advantageous Effects of Invention

According to the present invention, it is possible to provide an NDIR gas sensor and a gas analyzer having high responsiveness and less noise. Further, it is possible to provide a photosynthesis rate measuring apparatus having a short measurement time and high measurement accuracy and capable of being reduced in size. Further, the present invention can provide a photosynthesis rate measuring method having a short measurement time and high measurement accuracy.

BRIEF DESCRIPTION OF THE DRAWINGS

FIGS. 3A to 3B are diagrams for explaining an example of convection that occurs in a chamber.

FIGS. 4A to 4B are diagrams for explaining another example of the convection that occurs in the chamber.

Each of FIGS. 6A to 6C is a cross sectional view perpendicular to the route of the infrared ray of the sample cell according to another embodiment.

DESCRIPTION OF EMBODIMENTS

An NDIR sensor, a gas analyzer, a photosynthesis rate measuring apparatus, and a photosynthesis rate measuring method according to an embodiment of the present invention are explained below with reference to the accompanying drawings.

Figure 1A:
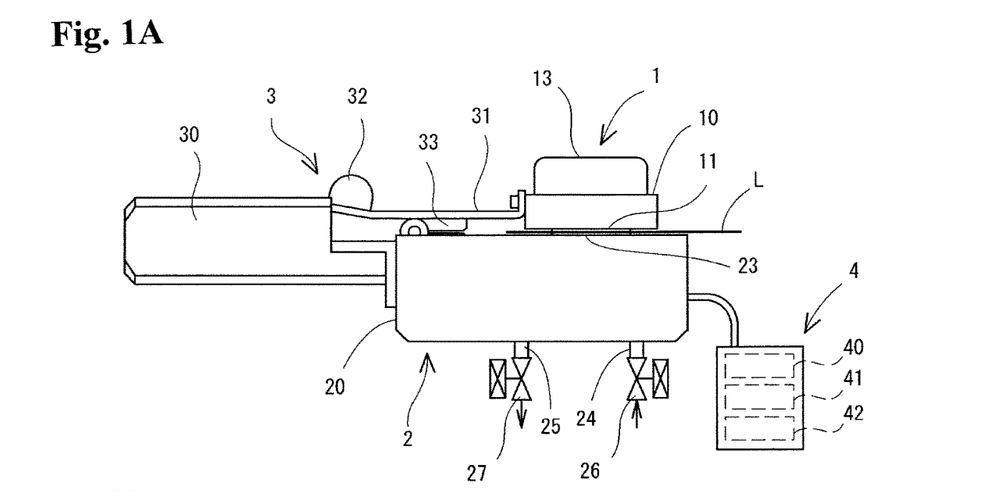
FIG. 1A is a front view of a photosynthesis rate measuring apparatus according to an embodiment and FIG. 1B is a front view for explaining a method of using the photosynthesis rate measuring apparatus.
Figure 1B:
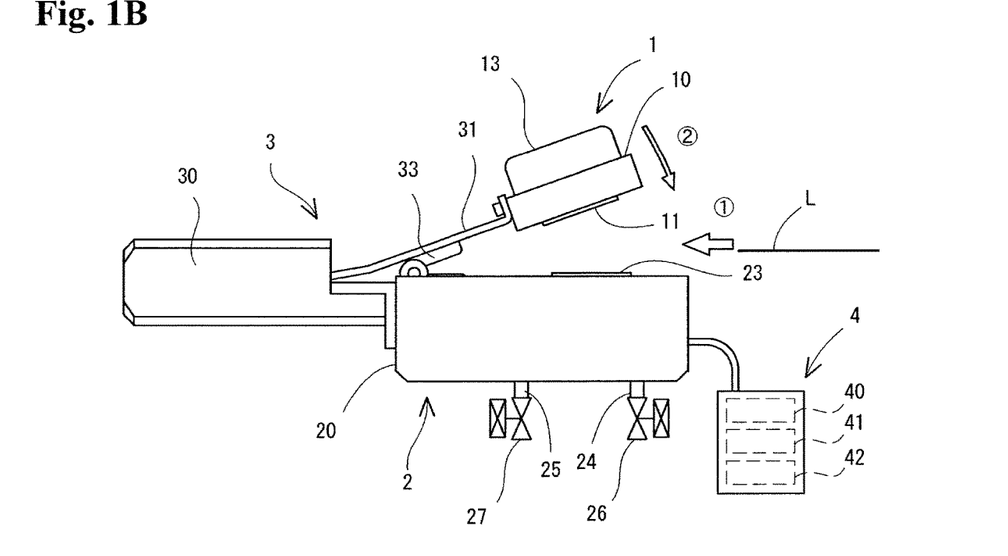
Figure 2A:
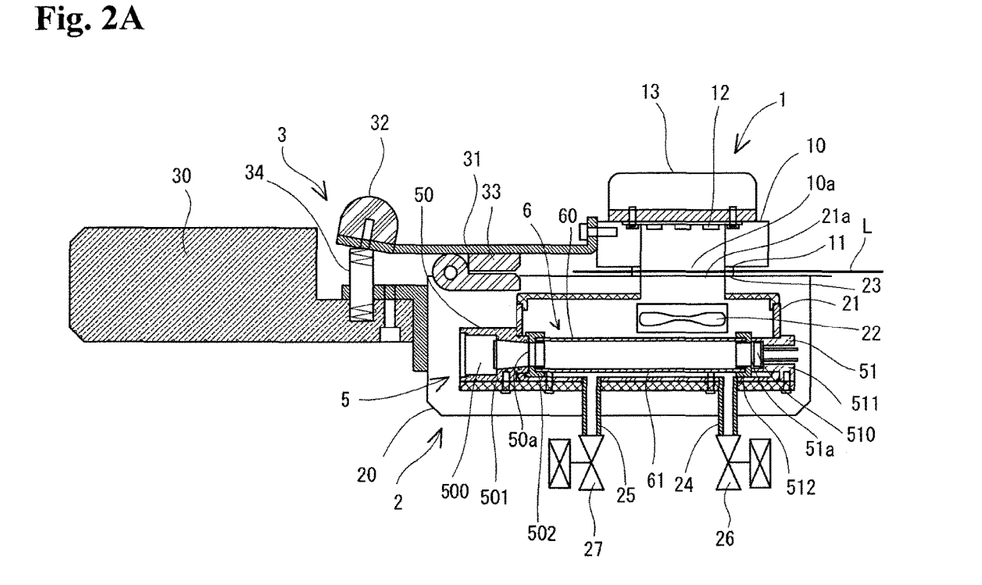
FIG. 2A is a front sectional view of a gas analyzer according to the embodiment and FIG. 2B is a side sectional view of the gas analyzer.
Figure 2B:
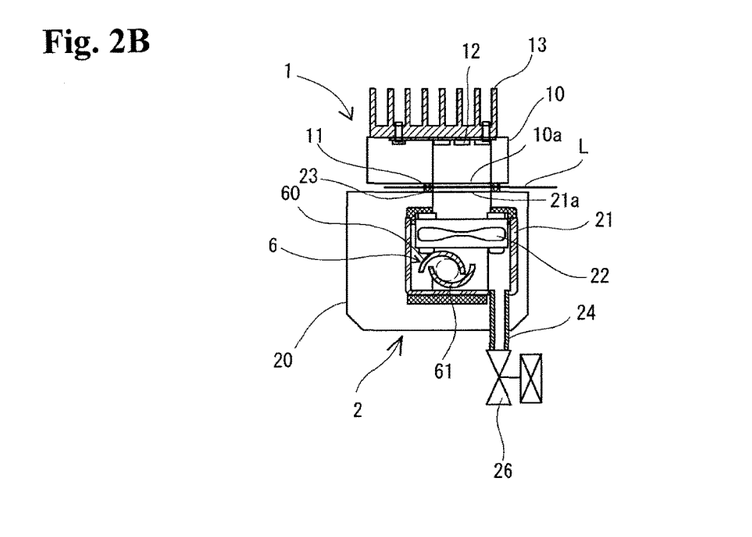

Referring to FIG. 1 and FIG. 2, the gas analyzer includes a light source unit 1, a chamber unit 2, and an operation unit 3. In the embodiment, the gas analyzer is a gas analyzer for measuring the concentration of $CO_2$ so as to measure a photosynthesis rate.

Referring to FIG. 2A and FIG. 2B, the light source unit 1 includes an upper case 10 including a downward square opening 10a. A gasket 11 is arranged along an edge of the opening 10a of the upper case 10.

The light source unit 1 includes a light source 12 arranged to radiate light for photosynthesis on a measurement leaf L. The light source 12 includes a plurality of LEDs. A light source other than the LEDs may be adopted. The light is visible light. The light may be monochromatic light or may be white light. The light source 12 is arranged on an upper part in the upper case 10 and radiates the light toward the opening 10a. When the measurement leaf L is sandwiched by the light source unit 1 and the chamber unit 2 as shown in FIG. 2, the light is radiated on the measurement leaf L from the light source 12. A heat radiation fin 13 is attached to the upper case 10 to be located behind the light source 12 and radiates heat generated by the light source 12.

As shown in FIG. 2, the chamber unit 2 includes a lower case 20, a sealable chamber 21 arranged in the lower case 20, a fan 22 arranged in the chamber 21, and an NDIR (non-dispersive infrared ray) gas sensor 5 (hereinafter simply referred to as gas sensor) according to the present invention provided for the chamber 21.

The chamber 21 includes an upward opening 21a to be closed by the measurement leaf L. The opening 21a has the same square shape as the opening 10a of the light source unit 1. A gasket 23 is arranged along an edge of the opening 21a. When the light source unit 1 is placed on the chamber unit 2, both the gaskets 11 and 23 are in contact with each other and both the openings 10a and 21a face each other. The size of each of the openings 10a and 21a is, for example, 2 cm×3 cm.

An introduction line 24 is connected to the chamber 21 so as to introduce gas such as the air into the chamber 21 from the outside. A not-shown pump is arranged to introduce the gas into the chamber 21 through the introduction line 24. A discharge line 25 is connected to the chamber 21 so as to discharge the gas from the chamber 21 to the outside. Further, an electromagnetic valve 26 is arranged to open and close the introduction line 24, and an electromagnetic valve 27 is arranged to open and close the discharge line 25. The opening 21a is closed by the measurement leaf L and both the lines 24 and 25 are closed by the valves 26 and 27, whereby the chamber 21 is sealed.

Figure 3A:
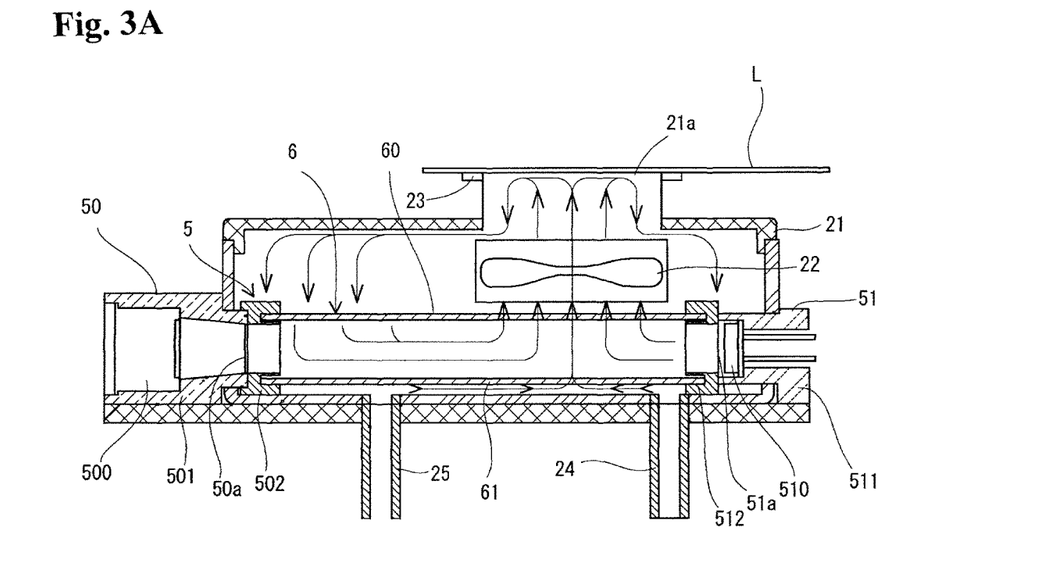
FIG. 3A is a main part front sectional view of the gas analyzer and FIG. 3B is a side sectional view of the gas analyzer.
Figure 3B:
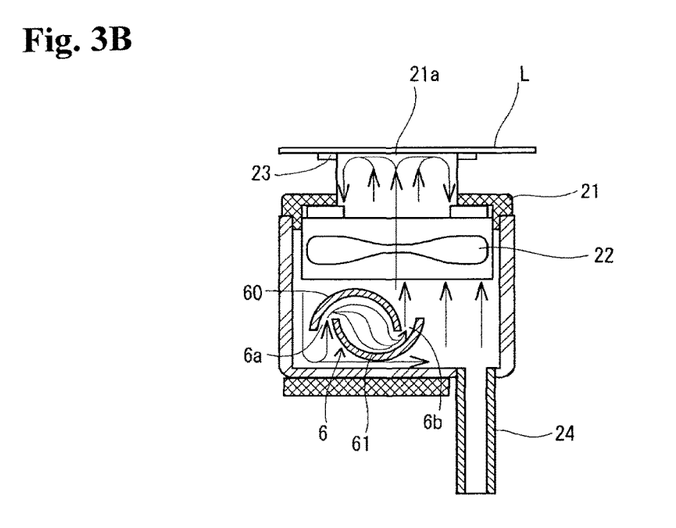
Figure 4A:
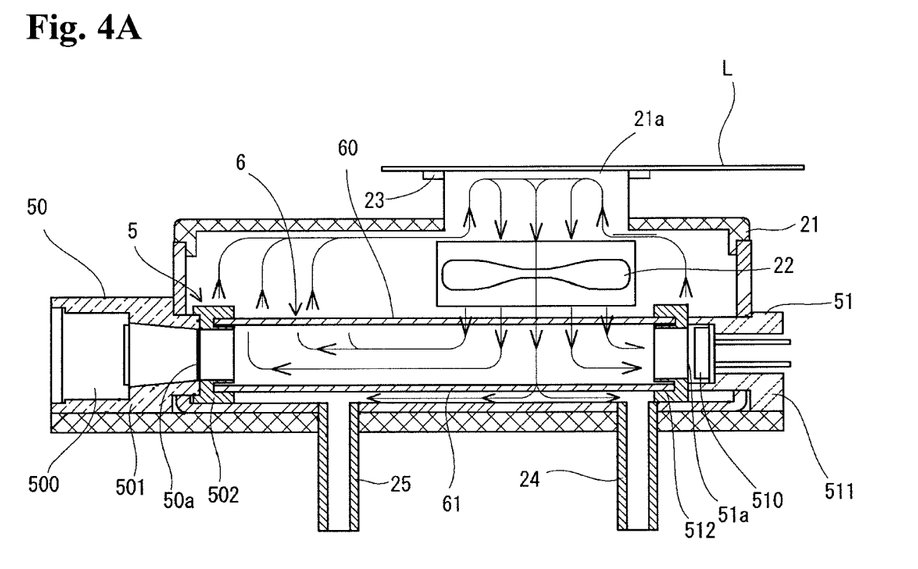
FIG. 4A is a main part front sectional view of the gas analyzer and FIG. 4B is a side sectional view of the gas analyzer.
Figure 4B:
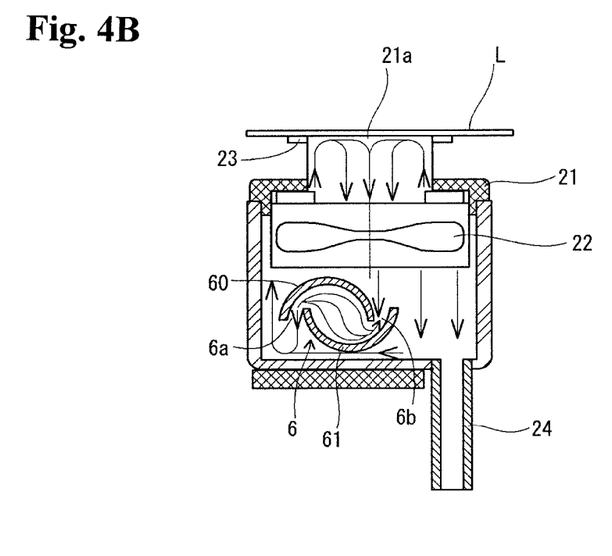

The fan 22 is a fan for circulating the gas in the chamber 21. The fan 22 is arranged right under the opening 21a and is located right under the measurement leaf L that closes the opening 21a. As shown in FIG. 3, the fan 22 may be arranged to generate an air current flowing toward the opening 21a, that is, to generate an air current flowing toward the measurement leaf L. As shown in FIG. 4, the fan 22 may be arranged to generate an air current flowing toward a direction opposite to the opening 21a. With the arrangement shown in FIG. 4, the gas in the vicinity of the opening 21a, that is, the gas right under the measurement leaf L is sucked by the fan 22.

In the embodiment, the gas sensor 5 is a gas sensor for measuring the concentration of $CO_2$ (a target gas) included in the gas (a sample gas) in the chamber 21. Referring to FIG. 3 or FIG. 4, the gas sensor 5 includes a radiating section 50 arranged to radiate an infrared ray and a detecting section 51 arranged to detect the infrared ray radiated by the radiating section 50. Further, the gas sensor 5 includes a sample cell 6 extending between the radiating section 50 and the detecting section 51 along a route of an infrared ray in the chamber 21, and covering the entire circumference of the route of the infrared ray.

The radiating section 50 includes an infrared light source 500 such as a filament heater that radiates an infrared ray and a case 501 that houses the infrared light source 500 and hermetically penetrates through a sidewall of the chamber 21. A circular passage port 50a, through which the infrared ray passes, is formed in the case 501.

The detecting section 51 includes a detector 510 that detects the infrared ray radiated from the infrared light source 500 through the sample cell 6 and a case 511 that houses the detector 510 and hermetically penetrates through the sidewall of the chamber 21. A circular passage port 51a, through which the infrared ray passes, is formed in the case 511. The radiating section 50 and the detecting section 51 are arranged such that the passage ports 50a and 51a are opposed to each other.

In the embodiment, the gas sensor 5 is a dual type. Two detectors 510 for measurement and for reference (only one of which is shown in the figure) are provided. A band-pass filter for measurement (not shown in the figure) is arranged in the pre-stage of the detector 510 for measurement and selectively transmits an infrared ray having a wavelength absorbed by the target gas. The infrared ray transmitted through the band-pass filter for measurement is detected by the detector 510 for measurement. A band-pass filter for reference (not shown in the figure) is arranged in the pre-stage of the detector 510 for reference and transmits an infrared ray having a wavelength not absorbed by the target gas. The infrared ray transmitted through the band-pass filter for reference is detected by the detector 510 for reference.

In this embodiment in which the target gas is $CO_2$, for example, the band-pass filters for measurement and reference are selected such that the detector 510 for measurement detects an infrared ray having a wavelength of 4.3 μm and the detector 510 for reference detects an infrared ray having a wavelength of 4.0 μm.

The gas sensor 5 includes a concentration calculating section 40 (FIG. 1) configured to calculate concentration of the target gas on the basis of a detection result of the detecting section 51. The concentration calculating section 40 includes a concentration calculation circuit that calculates gas concentration on the basis of a detection signal from the detector 510.

An infrared ray passes through the sample cell 6 and is then detected by the detectors 510 for measurement and for reference. At this time, in the sample cell 6, a part of the infrared ray is absorbed by the target gas included in the sample gas. Therefore, a detection signal output from the detector 510 for measurement changes depending on the concentration of the target gas. Consequently, it is possible to detect the target gas. The concentration of the target gas is calculated by the concentration calculation circuit on the basis of a detection signal from the detector 510 for measurement and a detection signal from the detector 510 for reference. Since gas concentration measurement itself by an NDIR method is well known, detailed explanation of the gas concentration measurement is omitted.

In the embodiment, the sample cell 6 includes a first cell element 60 and a second cell element 61. The cell elements 60 and 61 have semi-cylindrical shapes same as each other extending along a route of the infrared ray. As shown in FIG. 3A and FIG. 4A, one end of each of the cell elements 60 and 61 is supported by a window frame 502 of the radiating section 50. The other end of each of the cell elements 60 and 61 is supported by a window frame 512 of the detecting section 51. The window frames 502 and 512 allow passage of the infrared ray.

Figure 5A:
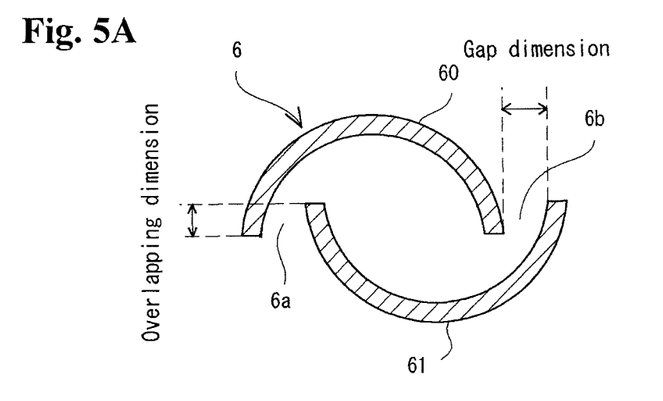
FIG. 5A is a cross sectional view perpendicular to a route of an infrared ray of a sample cell according to the embodiment and Each of FIGS. 5B to 5C is a cross sectional view perpendicular to a route of an infrared ray of a sample cell according to another embodiment.

As shown in FIG. 5A, cross section of each of the cell elements 60 and 61 orthogonal to the route of the infrared ray is circularly arcuate. Both the cell elements 60 and 61 are arranged to be opposed to each other and to be shifted from each other such that a first gap 6a and a second gap 6b are formed. One side portion of the first cell element 60 and one side portion of the second cell element 61 overlap at an interval from each other, whereby the first gap 6a is formed between the inner surface of the first cell element 60 and the outer surface of the second cell element 61 and extends along the route of the infrared ray. The other side portion of the first cell element 60 and the other side portion of the second cell element 61 overlap at an interval from each other, whereby the second gap 6b is formed between the outer surface of the first cell element 60 and the inner surface of the second cell element 61 and extends along the route of the infrared ray. The entire circumference of the route of the infrared ray is covered by the first cell element 60 and the second cell element 61.

Each of the cell elements 60 and 61 is made of stainless steel. The inner surface of each of the cell elements 60 and 61 is plated with gold so as to reduce a reflection loss of the infrared ray. The gold plating on the inner surfaces is performed after the inner surfaces are subjected to polishing treatment such as honing polishing or electrolytic polishing.

With the sample cell 6, as shown in FIG. 3 and FIG. 4, the gas in the chamber 21 is introduced into the sample cell 6 through the first gap 6a/the second gap 6b and flows out to the outside of the sample cell 6 through the second gap 6b/the first gap 6a. That is, the sample gas is instantaneously introduced into the inside of the sample cell 6 from a gap extending in the longitudinal direction of the circumferential surface of the sample cell 6. Consequently, high responsiveness is obtained. Moreover, although the gaps 6a and 6b are formed, it is extremely hard for environmental light to enter the sample cell 6, since the circumference of the route of the infrared ray is entirely covered by a combination of the cell elements 60 and 61. Therefore, noise is little and measurement accuracy is maintained.

As it is evident from FIG. 5A, an overlapping dimension and a gap dimension can be adjusted by shifting the first cell element 60 and the second cell element 61. The gap dimension and the overlapping dimension of the sample cell 6 are appropriately selected according to the total length of the sample cell 6, the volume of the chamber 21, the performance of the fan 22, and the like. As an example, when the length of the sample cell 6 is 80 mm to 90 mm, the gap dimension is 1 mm to 3 mm and the overlapping dimension is 3 mm to 5 mm.

Referring to FIG. 2 again, the operation unit 3 includes a grip 30 attached to the lower case 20 of the chamber unit 2, an arm 31, one end of which is attached to the upper case 10 of the light source unit 1, a knob 32 attached to the other end of the arm 31, a hinge 33 attached to the arm 31 and the lower case 20, and a spring 34 arranged between the other end of the arm 31 and the grip 30.

When the grip 30 is gripped by a measurer and the knob 32 is pushed down together with the other end of the arm 31 against the spring 34, the light source unit 1 is separated from the chamber unit 2 as shown in FIG. 1B. The measurement leaf L is inserted between the units 1 and 2. Subsequently, when the push-down of the knob 32 is released, the measurement leaf L is sandwiched by the units 1 and 2 as shown in FIG. 1A. In this way, the measurer can easily perform measurement work with one hand using the operation unit 3.

The gas analyzer includes a not-shown power supply unit arranged to supply electric power to the light source 12 of the light source unit 1, the fan 22 of the chamber unit 2, and the gas sensor 5. The power supply unit includes a battery.

Use of the gas analyzer is explained below.

The operation unit 3 is operated by the measurer and the measurement leaf L is sandwiched between the light source unit 1 and the chamber unit 2. At this time, the surface of the measurement leaf L is directed to the light source unit 1 and the rear surface of the measurement leaf L is directed to the chamber unit 2. Further, the openings 10a and 21a are closed by the measurement leaf L.

The gas analyzer opens the introduction line 24 and the discharge line 25 with the valves 26 and 27, introduces gas such as the air into the chamber 21 from the outside with the pump, and actuates the fan 22 to fill the chamber 21 with the introduced gas. Subsequently, the gas analyzer seals the chamber 21 by closing the lines 24 and 25 with the valves 26 and 27.

Subsequently, the gas analyzer radiates light on the surface of the measurement leaf L from the light source 12 of the light source unit 1 to causes the measurement leaf L to perform photosynthesis. The gas analyzer measures $CO_2$ concentration in the chamber 21 with the gas sensor 5 while causing the measurement leaf L to perform the photosynthesis and circulating the gas in the chamber 21 with the fan 22.

In the photosynthesis, the measurement leaf L absorbs $CO_2$ in the gas in the chamber 21 from stomas on the rear surface of the measurement leaf L. Therefore, the $CO_2$ concentration in the chamber 21 starts to decrease. As shown in FIG. 3 and FIG. 4, the gas is circulated in the chamber 21 by the fan 22 and instantaneously introduced into the sample cell 6. Therefore, the $CO_2$ concentration in a sealed space being reduced by the photosynthesis of the measurement leaf L is measured by the gas sensor 5 substantially on a real-time basis.

As explained above, because of the configuration of the sample cell 6, the gas analyzer can measure the $CO_2$ concentration being reduced by the photosynthesis substantially on a real-time basis and with high accuracy. As explained below, the photosynthesis rate measuring apparatus measures a photosynthesis rate on the basis of a temporal change of the $CO_2$ concentration according to a photosynthesis rate measuring method explained below.

As shown in FIG. 1, the photosynthesis rate measuring apparatus includes the gas analyzer arranged to measure the $CO_2$ concentration being reduced by the photosynthesis of the measurement leaf L and a temperature sensor (not shown in the figure) arranged to measure the temperature in the chamber 21. Further, the photosynthesis rate measuring apparatus includes a recording section 41 and a rate calculating section 42. A calculation unit 4 is configured by the concentration calculating section 40, the recording section 41, and the rate calculating section 42.

The recording section 41 is a data logger and records, as measurement data, a temporal change of the $CO_2$ concentration calculated by the concentration calculating section 40. The rate calculating section 42 includes a rate calculation circuit or a rate calculation program and calculates a photosynthesis rate of the measurement leaf L on the basis of a temporal change of the $CO_2$ concentration measured by the gas analyzer and the temperature in the chamber 21 measured by the temperature sensor.

Figure 7:
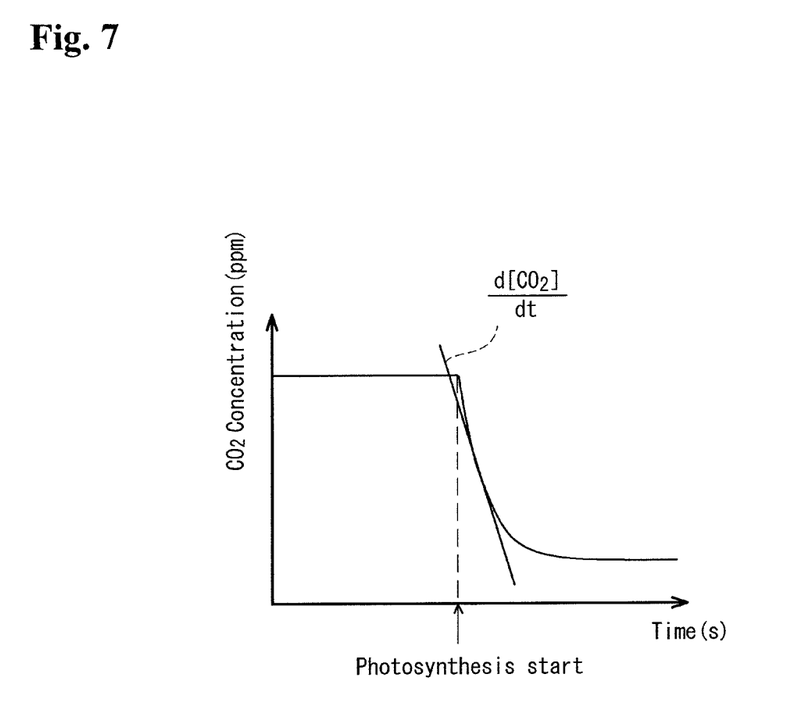
FIG. 7 shows a temporal change of $CO_2$ concentration in the chamber reduced by photosynthesis.

$CO_2$ concentration is not measured while the gas flows into the chamber 21 but measured while the chamber is kept sealed. Therefore, $CO_2$ concentration (ppm) in the chamber 21 drastically decreases simultaneously with a start of the photosynthesis of the measurement leaf L as shown in FIG. 7. A photosynthesis rate A ($molCO_2 \cdot m^{-2} \cdot s^{-1}$) can be calculated by the following Expression 1 derived by a temporal change $d[CO_2]/dt(ppm \cdot s^{-1})$ of the $CO_2$ concentration and an equation of state.

$$A = \left| \frac{d[CO_2]}{dt} \right| \times \frac{1.013 \times 10^5}{8.31 \times (273+T)} \times \frac{V}{S} \times 10^{-6} \quad \text{[Expression 1]}$$

The temporal change $d[CO_2]/dt(ppm \cdot s^{-1})$ of the $CO_2$ concentration is equivalent to a derived function of a curve shown in FIG. 7. In Expression 1, T(° C.) is a Celsius temperature in the chamber 21 and is measured by the temperature sensor. S ($cm^2$) is an area of the opening 21a closed by the measurement leaf L. V ($cm^3$) is a substantial volume of the chamber 21 excluding the fan 22, the gas sensor 5, the temperature sensor, and the like. V and S are known.

The $CO_2$ concentration in the chamber 21 being reduced by the photosynthesis of the measurement leaf L is measured by the gas sensor 5. Measurement data of the $CO_2$ concentration is recorded in the recording section 41. Specifically, the $CO_2$ concentration substantially linearly decreases for approximately 10 seconds from the start of the photosynthesis. Subsequently, the rate calculating section 42 calculates, from the measurement data recorded in the recording section 41, the temporal change $d[CO_2]/dt$ of the $CO_2$ concentration at a certain time point within approximately 10 seconds from the start of the photosynthesis. Subsequently, the rate calculating section 42 calculates, according to Expression 1 described above, the photosynthesis rate A of the measurement leaf L from the calculated temporal change $d[CO_2]/dt$ of the $CO_2$ concentration and temperature T in the chamber 21 measured by the temperature sensor.

As explained above, the photosynthesis rate measuring apparatus measures a photosynthesis rate in approximately 10 seconds from the start of the measurement (the start of the photosynthesis). The measured photosynthesis rate is displayed on a display.

As explained above, because of the high responsiveness and the less noise, the analyzer according to the present invention can measure $CO_2$ concentration in a sealed space being reduced by the photosynthesis of the measurement leaf L substantially on a real-time basis and accurately. Consequently, the apparatus and the method according to the present invention can accurately measure a photosynthesis rate. With the prior art shown in FIG. 10, there are a lot of disadvantages because the two gas analyzers 88 and 89 are required. On the other hand, in the present invention, only one gas analyzer is enough and flow rate control is not required. Since the measurement is performed on the basis of a temporal change of the $CO_2$ concentration drastically reduced in the sealed space, measurement accuracy is high.

A measurement time of a photosynthesis rate is approximately 10 seconds and is drastically reduced compared with the conventional system. The measurer can measure the photosynthesis rate only by sandwiching the measurement leaf L with the units 1 and 2 and waiting for approximately 10 seconds.

Since the $CO_2$ concentration in the sealed space is measured, the large pump, the flow-rate control section, and the flow meter necessary in prior art are not required. Therefore, it is possible to reduce the photosynthesis rate measuring apparatus in size and weight to be suitable for portable use. Further, it is possible to inexpensively provide the apparatus.

In countries such as Japan, an increase in production of crops is demanded so as to stably secure foods. Because of the improved efficiency of the measurement work for a photosynthesis rate according to the present invention, it is expected that researches and developments of breeds having high photosynthesis abilities and capable of being increased in production are accelerated.

The photosynthesis rate measuring apparatus is currently mainly used only in research sites. Since it is possible to provide an inexpensive photosynthesis rate measuring apparatus suitable for portable use, it is also expected that the apparatus spreads not only to the research sites but also to actual production sites and is used for crops cultivation diagnoses in fields. Further, this is considered to be an opportunity of a new agriculture image conforming to the IT introduction trend in agriculture in recent years.

[Responsiveness Confirmation Experiment of the Gas Analyzer]

Figure 8A:
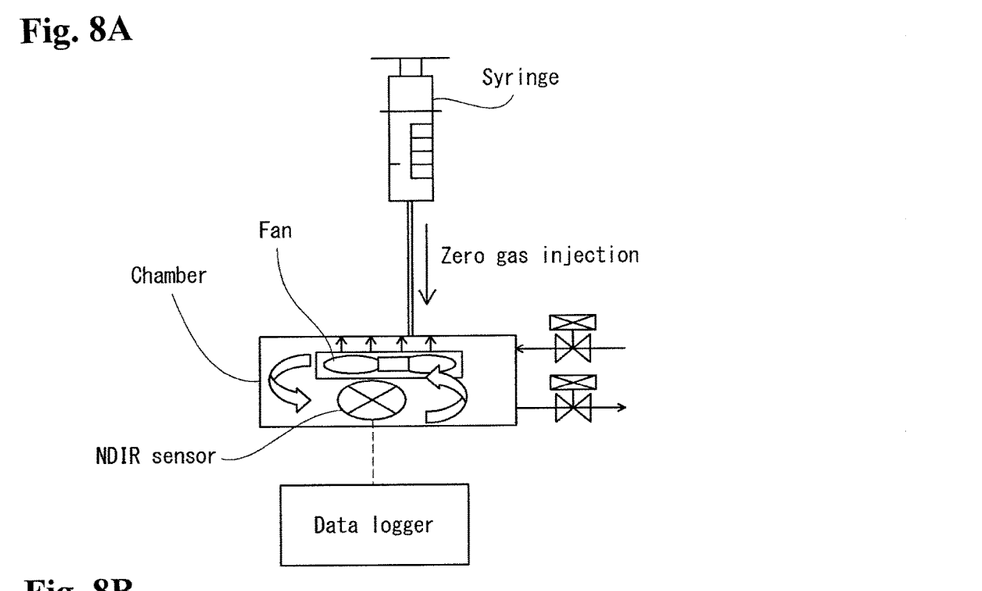
FIG. 8A schematically shows an experiment apparatus for confirming response speed of a gas sensor and FIG. 8B shows a temporal change of the $CO_2$ concentration in the chamber.
Figure 8B:
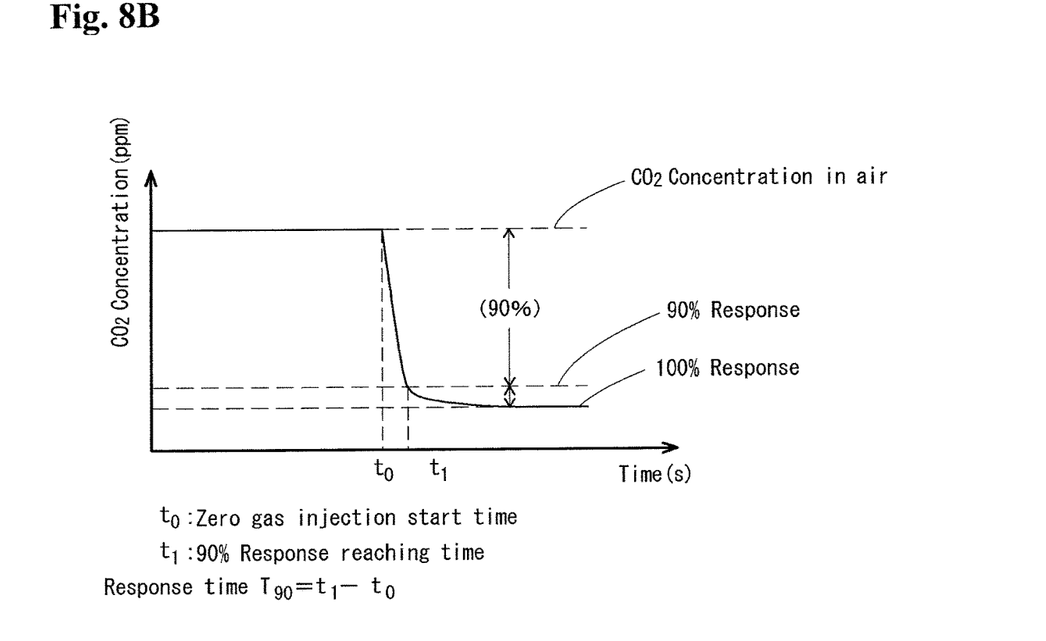

An experiment for confirming responsiveness of the gas analyzer was performed. As shown in FIG. 8A, a fan and an NDIR gas sensor were arranged in a chamber. A sample cell including a first cell element and a second cell element shown in FIG. 5A was used. In order to simulate a situation in which $CO_2$ concentration in the chamber is reduced by photosynthesis, after the air was filled in the chamber, gas not including $CO_2$ (hereinafter referred to as zero gas) was injected into the chamber from a syringe through a nozzle. A temporal change of the $CO_2$ concentration was measured by the gas sensor. Measurement data of the temporal change was recorded in a data logger. The recorded data was analyzed and, as shown in FIG. 8B, a 90% response time $T_{90}$ was calculated from measurement start time $t_0$ and time $t_1$ when response was 90%.

A sample cell length was 90 mm, a gap dimension was approximately 2 mm, and an overlapping dimension was 5 mm. A substantial volume in the chamber was approximately 90 ml. The zero gas was 10 ml. $T_{90}$ at the time when an injection time was set to 3.5 seconds and $T_{90}$ at the time when the injection time was set to 7.0 seconds were respectively calculated. A result of the calculation is shown in the following table T1.

TABLE 1

| Inject zero gas 10 ml | | |
|---|---|---|
| | Injection speed (ml/s) | Response time $T_{90}$ (s) |
| Injection time 3.5 (s) | 2.9 | 3.2 |
| Injection time 7.0 (s) | 1.4 | 8.0 |

As it is evident from Table 1, an injection time and a response time $T_{90}$ were approximate and high responsiveness was obtained even if injection speed was changed. It was confirmed that the $CO_2$ concentration being reduced in the sealed space was able to be measured substantially on a real-time basis. The high responsiveness is achieved by the circulation of the gas by the fan and the quick introduction of the sample gas from the gap on the sample cell side surface.

The preferred embodiment of the present invention is explained above. However, the present invention is not limited to the embodiment explained above.

The gas sensor 5 may measures concentration of other gasses than $CO_2$. The gas sensor 5 may be used not only for the concentration measurement of gas but also for gas detection. That is, the gas sensor 5 may be used to detect whether the target gas is included in the sample gas. The target gas may be gas other than carbon dioxide, for example, carbon monoxide, steam, methane, propane, ethylene, fron gas, nitrous oxide, or sulfur hexafluoride.

The gas sensor 5 is the dual type but may be a single type not including the detector 510 for reference. The gas sensor 5 may include a plurality of detectors for measurement and detect two or more kinds of target gasses or measure concentrations of the target gases. Water vapor generated in the chamber 21 by photosynthesis affects measurement of a photosynthesis rate. Therefore, the gas sensor 5 may measure not only the $CO_2$ concentration but also $H_2O$ concentration. The influence of the water vapor may be corrected on the basis of the measured $H_2O$ concentration.

Figure 5B:
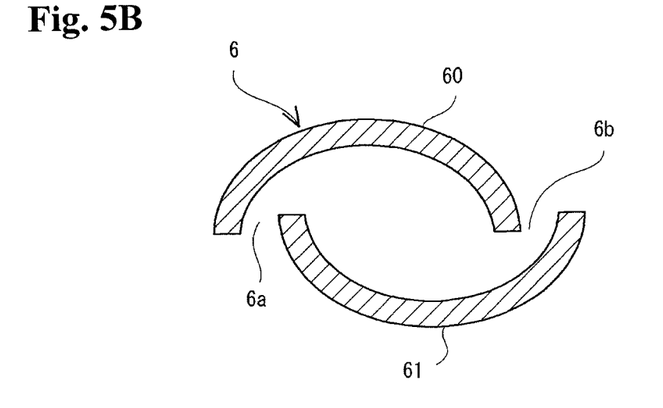
Figure 5C:
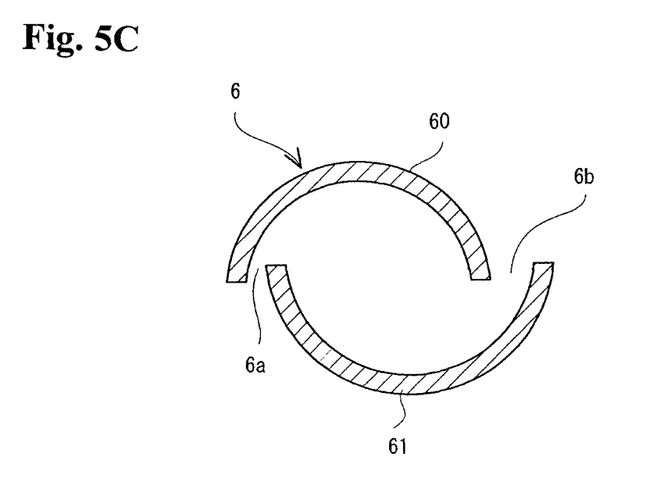
Figure 6A:
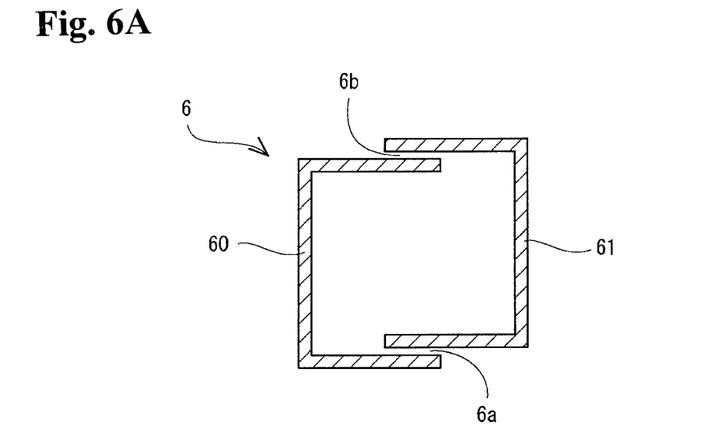
Figure 6B:
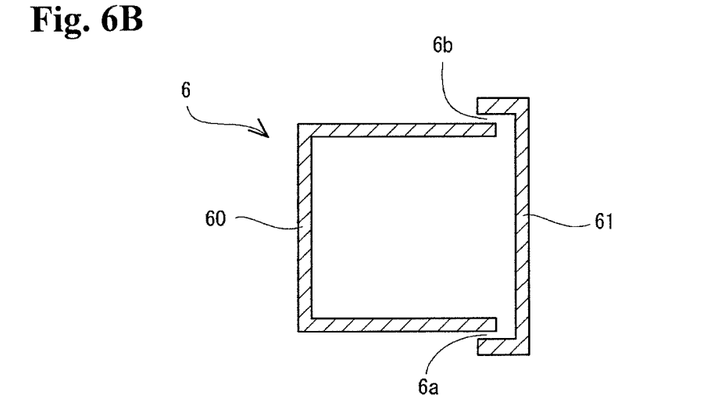
Figure 6C:
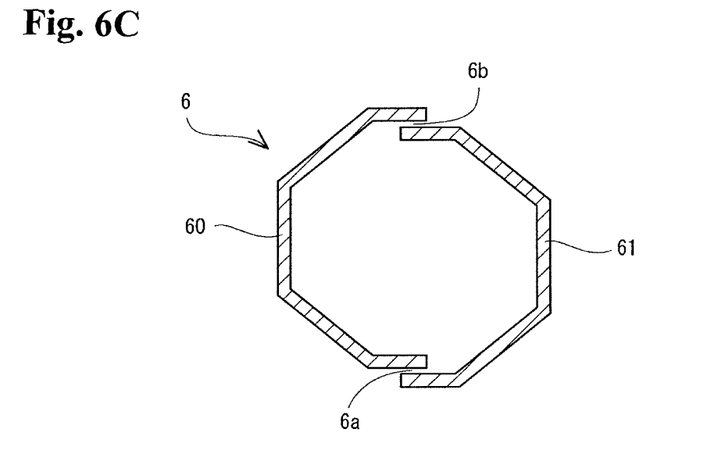

As shown in FIG. 5B and FIG. 5C in addition to FIG. 5A, the sample cell 6 may include the cell elements 60 and 61, the cross sections of which are arcuate, and may have a substantially circular cylindrical shape or a substantially elliptical cylindrical shape extending along the route of the infrared ray. The cell elements 60 and 61 shown in FIG. 5B have semielliptical cylindrical shapes same as each other. The cell elements 60 and 61 shown in FIG. 5C have semicylindrical shapes, the inner diameters of which are different from each other. As shown in FIG. 6A to FIG. 6C, the sample cell 6 may include the cell elements 60 and 61, the cross sections of which are bent in a substantially arcuate shape and may have a substantially polygonal cylindrical shape extending along the route of the infrared ray. The sample cell 6 shown in FIG. 6A and FIG. 6B has a substantially square cylindrical shape. The sample cell 6 shown in FIG. 6C has a substantially octagonal cylindrical shape. The polygonal cylindrical sample cell 6 may be configured from the cell elements 60 and 61 having the shapes same as each other as shown in FIG. 6A and FIG. 6C or may be configured from the cell elements 60 and 61 having the shapes different from each other as shown in FIG. 6B. The sample cell 6 is not limited to the illustrations in FIG. 5 and FIG. 6.

The sample cell 6 may include three or more cell elements. It is obvious that both of the high responsiveness and the less noise are obtained by the three or more cell elements. In other words, the sample cell 6 only has to be a sample cell in which the entire circumference of a route of an infrared ray is covered by a plurality of cell elements, side portions of the cell elements adjacent to each other overlap at an interval from each other, and a gap extending along the route of the infrared ray is formed between the outer surface/the inner surface of one cell element of the cell elements and the inner surface/the outer surface of the other cell element.

For more accurate concentration measurement, it is preferable that the infrared ray can be efficiently transmitted from the radiating section 50 to the detecting section 51. For example, the radiating section 50 may include a condensing lens for condensing the infrared ray from the infrared light source 500 toward a light receiving surface of the detector 510 to reduce a loss of the infrared ray due to reflection on the sample cell 6. Each of the cell elements may be made of another kind of metal instead of stainless steel or may be made of another material such as plastic or glass. Each of the cell elements may have mirror-finished inner surface or inner surface applied with an aluminum sheet instead of the inner surface plated with gold.

If the light receiving surface of the detector 510 is smaller than the diameter of the passage ports 50a and 51a, a part of the infrared ray deviates from the light receiving surface of the detector 510. In order to reduce such a loss of the infrared ray, the sample cell 6 may have a shape tapered from the radiating section 50 toward the detecting section 51. The tapered sample cell 6 can be configured by a plurality of cell elements gradually narrowed from the radiating section 50 toward the detecting section 51. It is more preferable that the tapered sample cell 6 and the condensing lens are combined.

Figure 9:
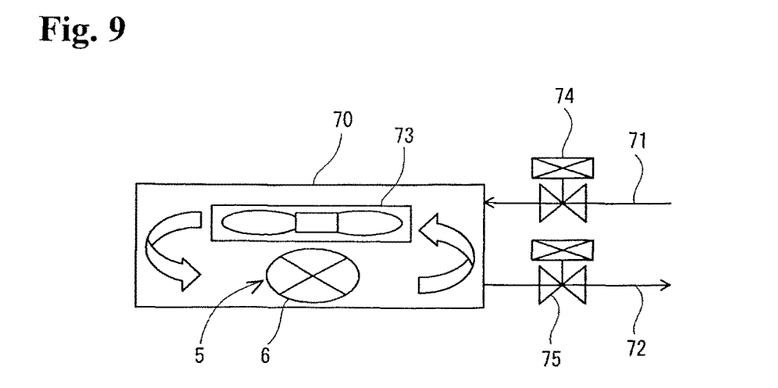
FIG. 9 schematically shows a gas analyzer according to another embodiment.

The gas analyzer may be used for a use other than the photosynthesis rate measurement. In FIG. 9, a gas analyzer according to another embodiment for detecting gas or measuring gas concentration is shown. The gas analyzer includes a chamber 70, an introduction line 71 connected to the chamber 70 so as to introduce a sample gas into the chamber 70, and a discharge line 72 connected to the chamber 70 so as to discharge the sample gas from the chamber 70. Further, the gas analyzer includes a pump (not shown in the figure) for introducing the sample gas from a supply source into the chamber 70 through the introduction line 71, and a fan 73 arranged in the chamber 70 to circulate the sample gas in the chamber 70. Further, the gas analyzer includes at least one NDIR gas sensor 5. The sample cell 6 of the gas sensor 5 is arranged in the chamber 70. The gas sensor 5 detects a target gas included in the sample gas in the chamber 70 or measures the concentration of the target gas.

In the analyzer, the detection or the concentration measurement of the target gas by the gas sensor 5 may be performed while introducing the sample gas into the chamber 70 from the supply source at a constant flow rate. Instead of this, the detection or the concentration measurement of the target gas may be performed while circulating the sample gas in the chamber 70 by the fan 73 after introducing the sample gas into the chamber 70 from the supply source and then sealing the chamber 70 by closing both the lines 71 and 72 with electromagnetic valves 74 and 75. The latter method is effective when an amount of the sample gas is small.

The photosynthesis rate may be measured as explained below. Referring to FIG. 2B, actually, the photosynthesis is performed not only on the rear surface of the measurement leaf L but also on the front surface of the measurement leaf L. That is, the measurement leaf L absorbs $CO_2$ in the upper case 10 as well. Therefore, it is also possible that the upper case 10 is set as an upper chamber, the chamber 21 is set as a lower chamber, a communication line for communicating chambers 10 and 21 with each other is provided, and one sealable chamber is formed by the upper chamber 10, the lower chamber 21, and the communication line. $CO_2$ concentration in the chamber is measured while causing the measurement leaf L to perform the photosynthesis and circulating the gas to the entire lower chamber 21 and the entire upper chamber 10 with the fan 22 through the communication line. Subsequently, the photosynthesis rate is measured. At this time, in Expression 1 described above, S ($cm^2$) is a sum of an area of the opening 21a and an area of the opening 10a. V ($cm^3$) is a sum of respective substantial volumes of the chamber 21, the upper case 10, and the communication line.

REFERENCE SIGNS LIST 1 light source unit
12 light source
2 chamber unit
21 chamber 21a opening
22 fan
3 operation unit
4 calculation unit
40 concentration calculating section
42 rate calculating section
5 gas sensor
50 radiating section
51 detecting section
6 sample cell
60 first cell element
61 second cell element
6a first gap
6b second gap
L measurement leaf

The invention claimed is:

1. A gas analyzer used for measurement of a photosynthesis rate of a measurement leaf, the gas analyzer comprising:
a sealable chamber including an opening to be covered by the measurement leaf;
a fan arranged in the chamber to circulate gas in the chamber; and
an NDIR gas sensor arranged to measure $CO_2$ concentration in the chamber,
the NDIR gas sensor comprising:
a radiating section arranged to radiate an infrared ray;
a detecting section arranged to detect the infrared ray radiated by the radiating section; and
a sample cell arranged in the chamber and extending between the radiating section and the detecting section along a route of the infrared ray and covering an entire circumference of the route,
wherein:
the sample cell includes a first cell element and a second cell element extending along the route and opposed to each other to cover together the entire circumference of the route, one side portion of the first cell element and one side portion of the second cell element being opposed to each other to form therebetween a first gap as an inlet of the sample cell, the other side portion of the first cell element and the other side portion of the second cell element being opposed to each other to form therebetween a second gap an outlet of the sample cell, the first and second gaps extending along the route;
the opening of the chamber faces upward; and
the fan and the sample cell are arranged right under the opening of the chamber.

2. The gas analyzer according to claim 1, wherein the sample cell has a shape tapering down from the radiating section toward the detecting section.

3. The gas analyzer according to claim 1, wherein each of the first and second cell elements has an inner surface plated with gold or mirror-finished.

4. The gas analyzer according to claim 1, further comprising a light source arranged to radiate light on the measurement leaf.

5. The gas analyzer according to claim 1, wherein the gas sensor is arranged right under the fan.

6. The gas analyzer according to claim 1, wherein the fan is arranged in the chamber to generate an air current flowing toward the opening of the chamber.

7. The gas analyzer according to claim 1, wherein the fan is arranged in the chamber to generate an air current flowing toward a direction opposite to the opening of the chamber.

8. A photosynthesis rate measuring apparatus for measuring a photosynthesis rate of a measurement leaf, the photosynthesis rate measuring apparatus comprising:
the gas analyzer according to claim 1 arranged to measure $CO_2$ concentration being reduced by photosynthesis of the measurement leaf; and
a rate calculating section configured to calculate a photosynthesis rate of the measurement leaf on a basis of a temporal change of the $CO_2$ concentration measured by the gas analyzer.

9. A photosynthesis rate measuring method for measuring a photosynthesis rate of a measurement leaf, the photosynthesis rate measuring method comprising:
preparing the gas analyzer according to claim 1;
closing the opening of the chamber with the measurement leaf and sealing the chamber;
measuring $CO_2$ concentration in the chamber with the NDIR gas sensor while keeping the chamber sealed, causing the measurement leaf to perform photosynthesis and circulating gas in the chamber with the fan; and
calculating a photosynthesis rate of the measurement leaf on the basis of a temporal change of the measured $CO_2$ concentration.

10. The photosynthesis rate measuring method according to claim 9, wherein the photosynthesis rate of the measurement leaf is measured on the basis of the temporal change of the $CO_2$ concentration in the chamber within 10 seconds from a start of the photosynthesis by the measurement leaf.

* * * * *